United States Patent [19]

Nishizawa et al.

[11] Patent Number: 5,028,309

[45] Date of Patent: Jul. 2, 1991

[54] ELECTROCHEMICAL DEVICE INCORPORATING MEANS FOR PREVENTING REDUCTION OF SOLID ELECTROLYTE AND INSULATING CERAMICS DUE TO HEATER CURRENT LEAKAGE

[75] Inventors: Hitoshi Nishizawa, Iwakura; Yoshihiko Mizutani; Kazuyoshi Shibata, both of Nagoya, all of Japan

[73] Assignee: NGK Insulators, Ltd., Japan

[21] Appl. No.: 312,750

[22] Filed: Feb. 21, 1989

[30] Foreign Application Priority Data

Feb. 22, 1988 [JP] Japan .................................. 63-39089

[51] Int. Cl.$^5$ ............................................ G01N 27/41
[52] U.S. Cl. .................................... 204/425; 204/408; 204/412; 204/426; 204/428
[58] Field of Search ..................... 204/153.18, 421–429

[56] References Cited

U.S. PATENT DOCUMENTS

| | | | |
|---|---|---|---|
| 4,559,126 | 12/1985 | Mase et al. | 204/425 |
| 4,634,514 | 1/1987 | Nishizawa et al. | 204/425 |
| 4,657,659 | 4/1987 | Mase et al. | 204/426 |
| 4,728,411 | 3/1988 | Mase et al. | 204/428 |
| 4,798,693 | 1/1989 | Mase et al. | 204/427 |

*Primary Examiner*—T. Tung
*Attorney, Agent, or Firm*—Parkhurst, Wendel & Rossi

[57] ABSTRACT

An electrochemical device having an oxygen-ion conductive solid electrolyte body, a plurality of electrodes formed on the solid electrolyte body, an electrically insulating ceramic layer formed on the solid electrolyte body, a heater disposed such that the heater is electrically insulated by the ceramic layer from the solid electrolyte body, and a dc power source electrically connected to the heater for energizing the heater. At least one of the electrodes is electrically connected to a low-potential terminal of the dc power source. A voltage source is connected in a line between the above-indicated at least one electrode and the low-potential terminal of the dc power source, so that a potential of each of the at least one electrode with respect to a potential V1 at a point of connection of the above-indicated line to the low-potential terminal of the dc power source is maintained at a positive value which satisfies a formula, $V1 \leq V2 + V3$, where V2 represents voltage drop between a low-potential terminal of a heat-generating portion of the heater and the point of connection to the low-potential terminal of the dc power source, which occurs due to the heating current applied to the heat-generating portion, and V3 represents decomposition potential of the ceramic layer or the solid electrolyte body, whichever is lower, where the at least one electrode operates as an anode.

10 Claims, 4 Drawing Sheets

ELECTROCHEMICAL DEVICE INCORPORATING MEANS FOR PREVENTING REDUCTION OF SOLID ELECTROLYTE AND INSULATING CERAMICS DUE TO HEATER CURRENT LEAKAGE

BACKGROUND OF THE INVENTION

1. Field of the Invention

The present invention relates in general to an electrochemical device, and more particularly to an electrochemical device with an electrochemical element having an electrochemical cell which includes a solid electrolyte body and a heater formed integrally with the cell.

2. Discussion of the Prior Art

An electrochemical device which uses a zirconia oxygen-ion conductive solid electrolyte body and operates according to the principle of an oxygen concentration cell is known as an oxygen sensor for measuring or determining the concentration of oxygen in exhaust gases emitted by a vehicle internal combustion engine, or in combustion gases in industrial furnaces and boilers. In the art of controlling the combustion of an air-fuel mixture in an internal combustion engine for a motor vehicle, for example, the oxygen concentration in the exhaust gases is generally detected by such an electrochemical oxygen sensing device, in order to determine the air/fuel ratio of the air-fuel mixture which has a known relationship with the oxygen concentration. Based on the determined air/fuel ratio of the air-fuel mixture, an amount of supply of the fuel to the engine is controlled in a feedback manner, for accurately maintaining the air/fuel ratio of the mixture at an optimum level.

Usually, it is required to provide such an electrochemical device with a suitable heater to maintain the electrodes and solid electrolyte body of an electrochemical cell of the sensing element at an optimum elevated operating temperature, so that the electrochemical device may be operated so as to exactly determine the oxygen concentration of a gas to be measured, even when the temperature of the measurement gas is comparatively low. An example of a heater-built-in electrochemical element is disclosed in U.S. Pat. No. 4,300,990, wherein a heater layer incorporating a heat-generating element is formed on one of opposite major surfaces of an electrochemical cell consisting of a solid electrolyte body and a plurality of electrodes, such that the heat-generating element produces heat for heating at least a portion of the cell at which the electrodes are disposed.

Described more specifically, a heater-built-in electrochemical element as indicated above includes a planar body of an oxygen-ion conductive solid electrolyte, a plurality of electrodes formed on the planar solid electrolyte body, an electrically insulating ceramic layer formed on the planar solid electrolyte body, and a heater layer which is electrically insulated from the solid electrolyte body by the ceramic layer. The heat-generating element of the heater layer is connected to a dc voltage source of 10-20 V so that a heater current is applied to energize the heat-generating element, whereby the electrochemical element is heated by heat produced by the energized heat-generating element. For example, the electrochemical element is heated to a temperature not lower than about 300° C. At this high temperature, the current applied to the heat-generating element may leak from a high-potential terminal of the heat-generating element into the solid electrolyte body, through the insulating ceramic layer, and back to a low-potential terminal of the heat-generating element, again through the insulating ceramic layer. This leak current causes reduction and consequently deterioration of a portion of the insulating ceramic layer adjacent to the low-potential terminal of the heat-generating element, and a portion of the solid electrolyte body which contacts the above-indicated portion of the ceramic layer. Thus, the known heater-built-in electrochemical element suffers from shortened life expectancy due to such deterioration of the ceramic layer and solid electrolyte body.

In view of the above problem of the heater current leakage and resultant reduction in the service life of the heater, it has been proposed to electrically connect one of the electrodes on the solid electrolyte body, to the low-potential terminal of the dc power supply for the heater as disclosed in U.S. Pat. Nos. 4,798,693 and 4,728,411. While this arrangement prevents the conventionally experienced problem, the proposed wiring arrangement requires a bi-polar power source for the electrochemical cell (solid electrolyte body and electrodes) to be able to effect a bi-directional oxygen pumping operation. Accordingly, the cost of the electrical circuitry of the electrochemical device undesirably increases, where the electrochemical device is used in automotive vehicles or in other environments in which only a unipolar power source is available.

SUMMARY OF THE INVENTION

It is therefore an object of the present invention to provide an improved electrochemical device in which an electrode formed on a solid electrolyte body of an electrochemical element is electrically through voltage applying means to a low-potential terminal of a dc power source for a heater such that the potential of that electrode is maintained at a positive voltage with respect to that of the low-potential terminal of the dc power source, and which electrochemical device can be used for a prolonged period with high operating stability, without suffering from conventionally encountered deterioration of the solid electrolyte body and an electrically insulating layer which insulates the heater from the solid electrolyte body.

The above object may be achieved according to the principle of the present invention, which provides an electrochemical device having an oxygen-ion conductive solid electrolyte body, a plurality of electrodes formed on the solid electrolyte body, an electrically insulating ceramic layer formed on the solid electrolyte body, a heater disposed such that the heater is electrically insulated by the ceramic layer from the solid electrolyte body, and a dc power source electrically connected to the heater for energizing the heater, the electrochemical device being characterised in that at least one of the plurality of electrodes is electrically connected each as a first electrode to a low-potential terminal of the dc power source, and in that voltage applying means is provided in each of at least one line which connects a corresponding one of the first electrode and the low-potential terminal of the dc power source, so that a potential $V_1$ of the first electrode with respect to a potential at a point of connection of said each line to the low-potential terminal of the dc power source is maintained at a positive value which satisfies the following formula (1):

$$V1 \leq V2 + V3 \ldots \quad (1)$$

where,

V2: voltage drop between a low-potential terminal of a heat-generating portion of the heater and the point of connection of the at least one electrode to the low-potential terminal of the dc power source, which occurs due to the heating current applied to the heat-generating portion, V3: decomposition potential of the ceramic layer or the solid electrolyte body, whichever is lower, where, the at least one electrode operates as an anode.

In the electrochemical device of the present invention constructed as described above, the electrode or electrodes formed on the solid electrolyte body is/are connected to the low-potential terminal of the direct current power source for the heater, while the suitable voltage applying means is provided so that the potential V1 of the electrode of electrodes connected to the heater power source is a positive valve determined according to the formula (1). This arrangement protects the solid electrolyte body and the electrically insulating ceramic layer from deterioration due to otherwise possible reduction caused by otherwise possible leaking of the current applied to the heater. Thus, the instant electrochemical device may be used for a relatively long period of time.

Further, the instant electrochemical device may perform a bidirectional oxygen pumping operation, with a unipolar power source similar to that for the heater, since a pumping current may flow between the electrodes, through the solid electrolyte body, in opposite directions, while the potentials of the electrodes are held within a positive range, based on the positive potential V1 of the electrode(s) connected to the low-potential terminal of the dc power source.

In one preferred form of the present invention, suitable resistor means is provided between the low-potential terminal of said heat-generating portion of said heater and said point of connection of the above-indicated line to the low-potential terminal of said dc power source, so that a value of electrical resistance between the low-potential terminal of the heat-generating portion and the above point of connection is higher than that between a high-potential terminal of said heat-generating portion and a high-potential terminal of said dc power source, in order to increase the amount of voltage drop V2 (as defined above) between the low-potential terminal of the heat-generating portion and the above point of connection, which occurs due to the heating current applied to the heat-generating portion. The increase in the amount of voltage drop results in raising a level of a voltage that can be applied to the electrodes on the solid electrolyte body, while substantially protecting the solid electrolyte body and the electrically insulating ceramic layer against deterioration due to the leak current.

BRIEF DESCRIPTION OF THE DRAWINGS

The above and optional objects, features and advantages of the present invention will become more apparent by reading the following detailed description of presently preferred embodiments of the invention, when considered in conjunction with the accompanying drawings, in which.

DETAILED DESCRIPTION OF THE PREFERRED EMBODIMENTS

Figure 1:
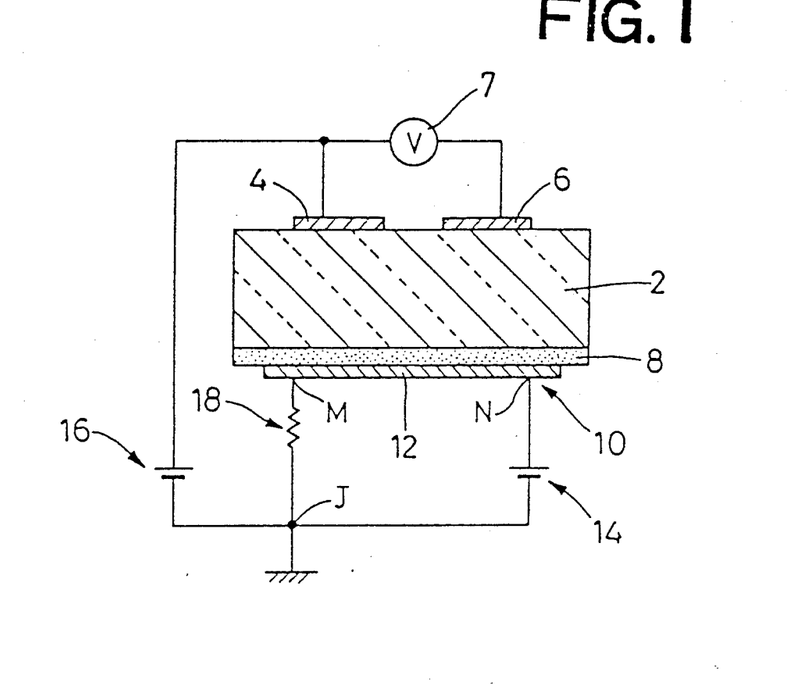
FIG. 1 is a schematic view illustrating a basic form of an electrochemical device according to the principle of the present invention.

Referring first to FIG. 1, reference numeral 2 denotes a solid electrolyte body made of an oxygen-ion conductive solid electrolyte material such as stabilized zirconia. On one of opposite major surfaces of this solid electrolyte body 2, there are integrally formed two electrodes 4, 6. The solid electrolyte body 2 and the electrodes 4, 6 cooperate with each other to form an electrochemical cell, which is operated according to the known principle of an oxygen concentration cell, to detect the oxygen concentration in a gas to be measured (hereinafter referred to as "measurement gas"). Reference numeral 7 designates high-input-impedance voltage detecting means connected in a line between the two electrodes 4, 6.

On the other major surface of the solid electrolyte body 2, there is integrally formed an electrically insulating ceramic layer 8 which is made of a suitable electrically insulating ceramic material such as alumina. A heat-generating portion in the form of a layer 12 of a heater 10 is formed on the ceramic layer 8 such that the heater 10 is electrically insulated by the ceramic layer 8 from the solid electrolyte body 2. The heat-generating layer 12 is energized by an electric current applied thereto from an external dc power source 14, whereby heat is generated by the layer 12, to heat the electrochemical cell, more precisely, at least an oxygen detecting portion of the solid electrolyte body 2 on which the electrodes 4, 6 are disposed. Thus, the oxygen detecting portion of the cell is maintained at a suitable operating temperature.

One of the two electrodes 4, 6 of the electrochemical cell, i.e., the first electrode 4 is electrically connected to a low-potential terminal of the dc power source 14 for the heater 10, at a point of connection J as indicated in FIG. 1. Further, voltage applying means in the form of an auxiliary power source 16 is connected in a line between the first electrode 4 and the connection point J. With the provision of this auxiliary power source 16, the potential V1 of the first electrode with respect to the connection point J is maintained at a positive value which satisfies the formula (1) given above. According to this arrangement, the potential of the solid electrolyte body 2 with respect to that of the electrically insulating ceramic layer 8 may be maintained at a suitable level, so as to effectively protect the solid electrolyte body 2 and ceramic layer 8 from otherwise possible deterioration due to reduction which may arise from a leak flow of the current applied to the heat-generating layer 12. In a line between a low-potential terminal M of the heat-generating layer 12 and the connection point J, there is provided a resistor 18 so that an amount of voltage drop between the terminal M and the connection point J, which occurs due to the heating current, is increased.

The decomposition potential or voltage of a solid electrolyte material or an electrically insulating ceramic material having an oxygen-ion conducting property is a potential at which an electrolysis current begins to increase appreciably. Described more specifically, the decomposition potential of the solid electrolyte or insulating ceramic material on which an anode and a cathode are formed in contact therewith is a level of an electromotive force at which a portion of the solid electrolyte or insulating ceramic material begins to be reduced, due to an increase in the electromotive force induced between the anode and cathode in the presence of a difference between oxygen concentrations of the atmospheres surrounding the anode and cathode, in other words, due to a decrease in the oxygen partial pressure of the atmosphere surrounding the cathode. The decomposition potential differs depending upon the oxygen partial pressure and temperature of the atmosphere to which the anode is exposed, and depending upon the composition of the solid electrolyte or insulating ceramic material.

For instance, the decomposition potential is considered to be a typical electrode potential obtained from a free energy Eo, where the oxygen partial pressure of the atmosphere to which the anode is exposed is almost one atmospheric pressure. Where the solid electrolyte is zirconia, the decomposition potential is 2.3 V at 800° C. Where the anode is exposed to the air, the decomposition potential of zirconia is almost equal to 2.3 V obtained where the oxygen partial pressure is one atmospheric pressure. Where the anode is exposed to a rich-burned exhaust gas (produced as a result of combustion of a fuel-rich air-fuel mixture) emitted by an internal combustion engine for a motor vehicle, the decomposition potential of zirconia is equal to 1.4 V. The decomposition potential of an electrically insulating ceramic material is substantially the same as that of the solid electrolyte, at an elevated temperature at which the ceramic material exhibits a predominantly high degree of oxygen-ion conductivity. For example, a typical decomposition potential of alumina at 800° C. is 2.3 V.

In the arrangement of FIG. 1 wherein the solid electrolyte body 2 and the electrically insulating ceramic layer 8 are formed as an integral structure, the decomposition potential of a portion of the solid electrolyte body 2 which contacts the ceramic layer 8 is important where the electron conductivity of the ceramic layer 8 is predominant over its oxygen-ion conductivity, since the electrode reaction at the interface between the solid electrolyte body 2 and ceramic layer 8 is restricted. On the other hand, where the oxygen-ion conductivity of the ceramic layer 8 is predominant over the electron conductivity, the decomposition potential of a portion of the ceramic layer 8 adjacent to the low-potential terminal M of the heat-generating layer 12 is important. Practically, however, these two decomposition potential values may not be clearly distinguished from each other, and therefore the decomposition potential V3 is generally interpreted to mean the lower one of the decomposition potentials of the solid electrolyte body 2 and ceramic layer 8.

As indicated in FIG. 1, the solid electrolyte body 2 and the electrically insulating ceramic layer 8 exist between the electrode 4 and the low-potential terminal M of the heat-generating layer 12 of the heater 10. When a voltage exceeding the decomposition potential of the ceramic layer 8 is applied between the opposite surfaces of the ceramic layer 8, the ceramic layer 8 is reduced and accordingly deteriorated. Further, when a voltage exceeding the decomposition potential of the solid electrolyte body 2 is applied to the interface between the solid electrolyte body 2 and the ceramic layer 8, the solid electrolyte body 2 is reduced and deteriorated. In view of this undesirable phenomenon, the voltage applying means, i.e., the auxiliary power source 16 is provided so that the potential of the electrode 4 with respect to that at the connection point J to the low-potential terminal of the heater power source 14 is controlled so as to protect the low-potential terminal M of the heat-generating layer 12 from a voltage which exceeds the decomposition potential V3, namely, so that the potential V1 of the electrode 4 is not higher than a sum of the decomposition potential V3, and the amount of voltage drop V2 between the low-potential terminal M of the heat-generating layer 12 and the connection point J, which occurs due to the heating current applied to the heater 10.

Where two or more electrodes are electrically connected to the low-potential terminal of the dc power source for the heater according to the present invention, an average potential of these electrodes is determined by a weighted averaging method. For instance, when the first and second electrodes are connected to the low-potential terminal of the heater power source, their potentials V11 and V12 may be determined so as to satisfy the following formula (2):

$$\frac{R2}{R1+R2} \cdot V11 + \frac{R1}{R1+R2}(V12 - Ve2) \leq V2 + V3 \quad (2)$$

where,

R1: sum of an electrical resistance of the solid electrolyte body between the first electrode and the electrically insulating ceramic layer, and an electrical resistance of an electric circuit between the first electrode and the low-potential terminal of the dc power source, R2: sum of an electrical resistance of the solid electrolyte body between the second electrode and the ceramic layer, and an electrical resistance of an electrical circuit between the second electrode and the low-potential terminal of the dc power source, Ve2 electromotive force induced between the first and second electrodes due to a difference between the oxygen partial pressures of the atmospheres to which the electrodes are exposed, the electromotive force being a positive value when the oxygen partial pressure of the atmosphere to which the second electrode is exposed is higher than the other.

According to the above formula (2), the potential of the solid electrolyte body which contacts the ceramic layer may be maintained at a suitable level.

In the basic form of the electrochemical device shown in FIG. 1, the second electrode 6 is electrically connected to the low-potential terminal of the dc power source 14 via voltage detecting means 7 which has a high input impedance. Therefore, R2 is much larger than R1, and the potential V1 of the first electrode 4 is almost equal to the decomposition potential V11 where only the first electrode 4 is connected to the low-potential terminal of the dc power source 14, as is understood from the following formula (3):

$$\frac{R2}{R1+R2} V11 + \frac{R1}{R1+R2} (V12 - Ve2) \approx V11 = V1 \quad (3)$$

Where three or more electrodes (number of the electrodes being represented by "n") are connected to the dc power source for the heater, the average potential V11, V12, ... V1n of the electrodes may be determined by a weighted averaging method, according to the following formula (4):

$$\frac{R}{R1} V11 + \sum_{i=1}^{n} \left\{ \frac{R}{Ri} (V1i - Vei) \right\} \leq V2 + V3 \quad (4)$$

where, $$R = \frac{1}{\sum_{i=1}^{n} \left( \frac{1}{Ri} \right)}$$

Figure 2:
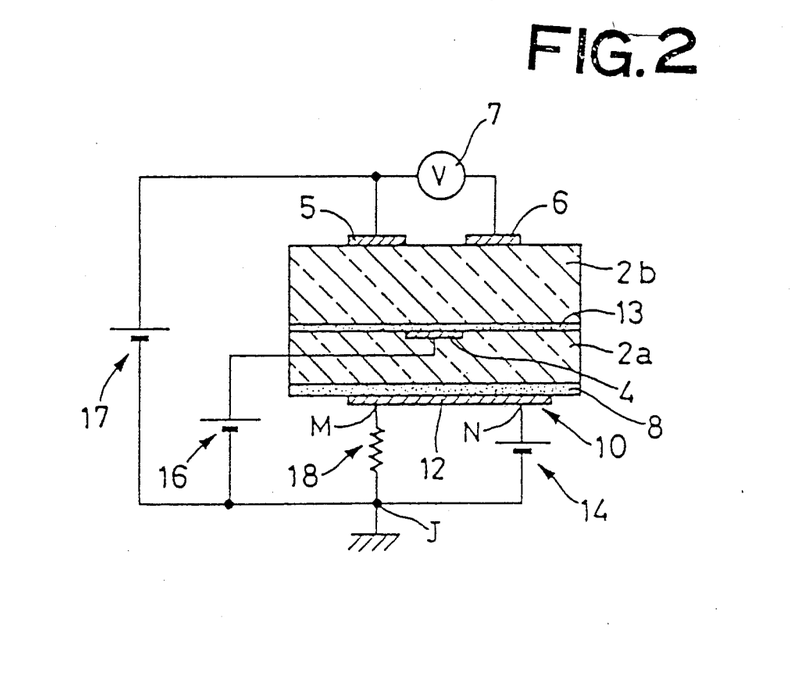
FIGS. 2 and 3 are schematic views of modifications of the basic form of the invention of FIG. 1.

Referring next to FIG. 2, there is illustrated an improvement of an electrochemical device disclosed in U.S. Pat. No. 4,814,059, wherein a solid electrolyte body consists of two parts 2a, 2b which are separated from each other by a second electrically insulating ceramic layer 13. A first electrode 4 is formed on a surface of the first solid electrolyte part 2a which contacts the second ceramic layer 13, while a second and a third electrode 5, 6 are formed on a surface of the second solid electrolyte part 2b which is remote from the ceramic layer 13. The solid electrolyte 2b and the second and third electrodes 5, 6 constitute an electrochemical cell, while the first electrode 4 serves as a protective electrode for preventing deterioration of the heater 10. In this arrangement, an electrical resistance of the solid electrolyte body 2a, 2b between the electrodes 5, 6 and the first electrically insulating ceramic layer 8 is comparatively large, in the presence of the second electrically insulating ceramic layer 13. Since R2 and R3 are much larger than R1, the following formula (5) is obtained according to the formula (4):

$$\frac{R2 \cdot R3 \cdot V11 + R3 \cdot R1 (V12 - Ve2) +}{R1 \cdot R2 + R2 \cdot R3 + R3 \cdot R1} \approx V11 = V1 \quad (5)$$

Therefore, an influence applied to the electrode 5 by voltage applying means 17 on the potential of the solid electrolyte 2a is very small. Accordingly, when the positive potential of the protective electrode 4 is set to V1, the potentials of the electrodes 5, 6 may be set to substantially any desired values.

Figure 3:
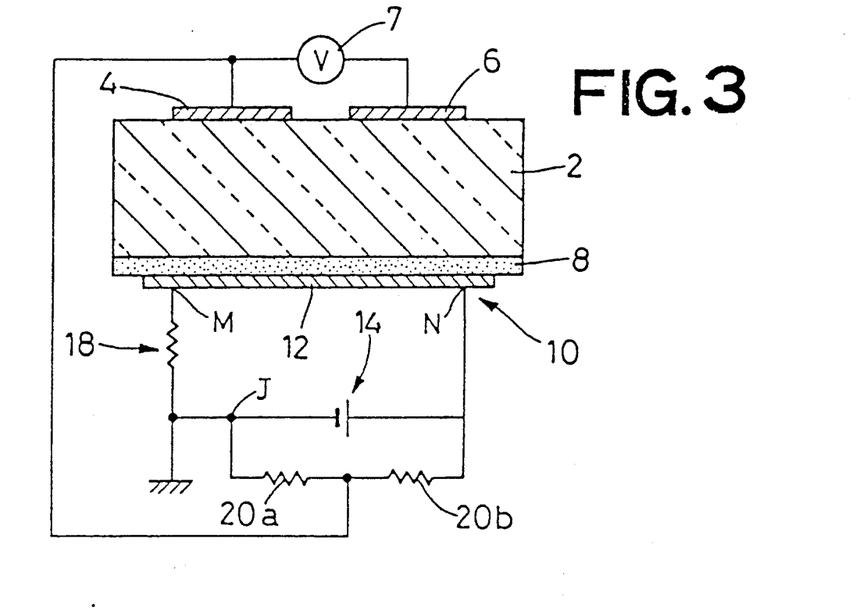

While the auxiliary power source 16 is used in the device of FIG. 1 as the voltage applying means for maintaining the potential of the first electrode 4 at a suitable value, the voltage applying means may take other forms. For instance, the dc power source 14 for the heater 10 may be utilized as the voltage applying means, as indicated in FIG. 3. Described in more detail, the voltage of the dc power source 14 is divided by voltage or potential dividing resistors 20a, 20b, so that a portion of the voltage is applied to the first electrode 4 such that the electrode 4 has a suitable positive potential with respect to the potential at the point of connection J to the low-potential terminal of the dc power source 14. Thus, a circuit including the heater power source 14 and the voltage dividing resistors 20a, 20b serves as the voltage applying means in the device of FIG. 3.

While some basic forms of the electrochemical device according to the principle of the present invention have been described by reference to FIGS. 1, 2 and 3, there will be described some presently preferred specific embodiments of the invention, referring to FIGS. 4-7.

Figure 4:
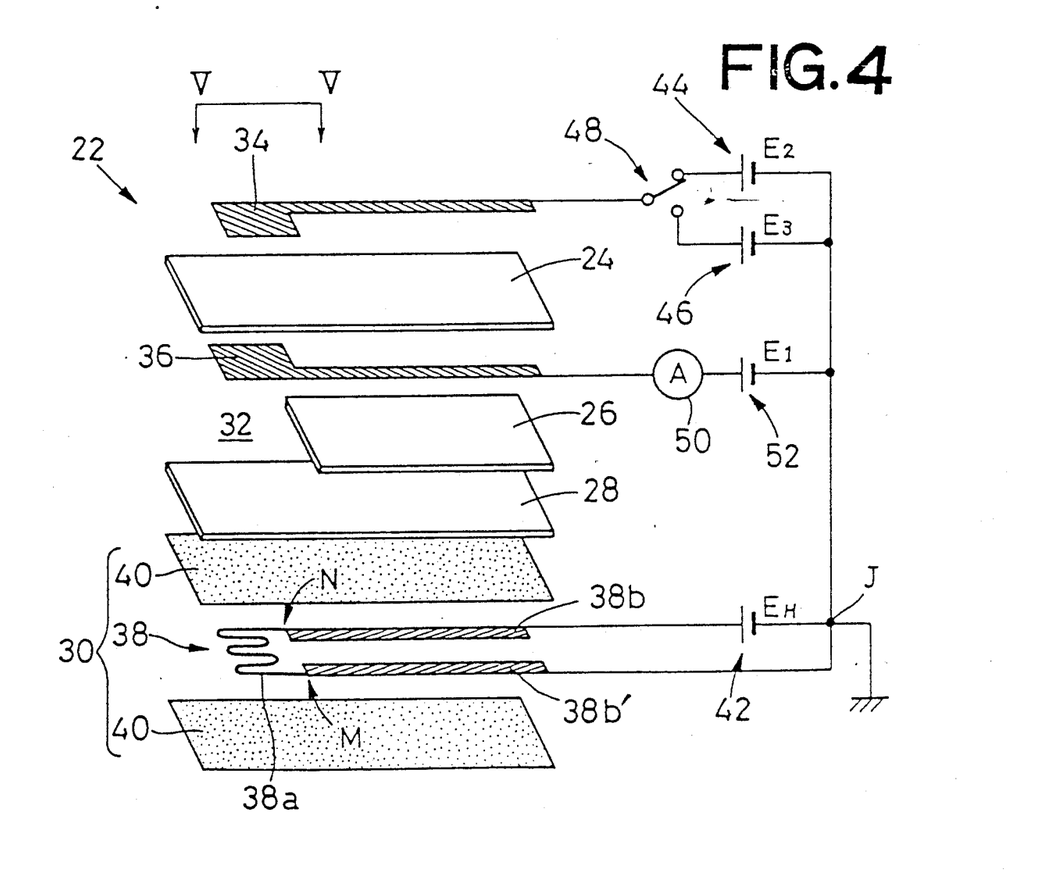
FIG. 4 is a schematic illustration consisting of an exploded perspective view of an electrochemical element used in one embodiment of the electrochemical device of the invention, and a diagram showing an electrical circuit of the element.
Figure 5:
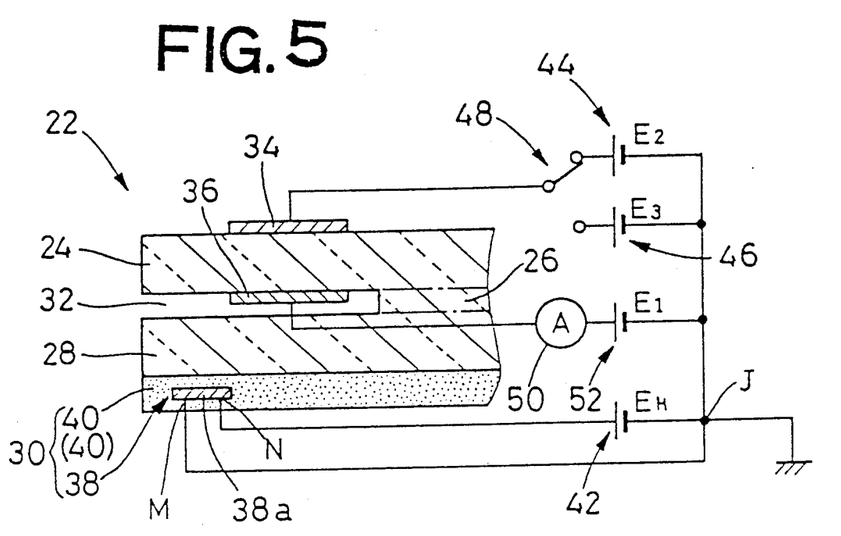
FIG. 5 is a schematic illustration consisting of a fragmentary elevational view in cross section taken along line V—V of FIG. 4, and the electrical circuit diagram of FIG. 4.

In FIGS. 4 and 5, an electrochemical element is indicated generally at 22. This element 22 has a generally elongate planar configuration, and includes an oxygen detecting portion formed at its distal end portion. The oxygen detecting portion operates to detect the oxygen concentration of a measurement gas, in a polarographic manner utilizing an oxygen pumping action, as described below.

As shown in FIGS. 4 and 5, the electrochemical element 22 has a laminar integral structure which includes a planar solid electrolyte body 24 formed of stabilized zirconia which exhibits oxygen-ion conductivity at an elevated temperature, spacer layers 26, 28 which are formed of a similar solid electrolyte material as the body 24, and a planar heater layer 30. The spacer layer 26 disposed between the solid electrolyte body 24 and the spacer layer 28 has a relatively small thickness, whereby a diffusion space in the form of a flat space 32 having a small thickness is formed between the solid electrolyte body 24 and the spacer layer 28, in communication with an external space in which the measurement gas exists. The thin flat space 32 has a suitable diffusion resistance to the measurement gas. On the outer surface of the solid electrolyte body 24, there is formed an outer pumping electrode 34 exposed to the external measurement gas. Further, an inner pumping electrode 36 is formed on a portion of the inner surface of the solid electrolyte body 24 which partially defines the thin flat space 32, such that the inner pumping electrode 36 is exposed to the thin flat space 32, and such that the two pumping electrodes 34, 36 are aligned with each other, in a plane parallel to the plane of the planar solid electrolyte body 24. The external measurement gas diffuses into the thin flat space 32, under the predetermined diffusion resistance, so that the inner pumping electrode 36 is exposed to the thus introduced measurement gas.

The heater layer 30 consists of a heater element 38 made of a mixture of platinum and zirconia, and a pair of electrically insulating ceramic layers 40, 40 which are formed of alumina such that the heater element 38 is sandwiched by and between the two alumina layers 40, 40. The heater element 38 consists of a heat-generating portion 38a which generates heat for heating the oxygen detecting distal end portion of the electrochemical element 22, and electrical leads 38b, 38b' which connect the heat-generating portion 38a to an external dc power source 42.

The solid electrolyte body 24 and the outer and inner pumping electrodes 34, 36 constitute an electrochemical pumping cell. To operate this pumping cell, a first pump power source 44 and a second pump power source 46 are selectively connected to the outer and inner pumping electrodes 34, 36, by means of a selector switch 48, so that a pumping current flows in a selected one of opposite directions, between the two pumping electrodes 34, 36. Namely, the pumping current flows either in the direction from the outer pumping electrode 34 toward the inner pumping electrode 36, or in the direction from the inner pumping electrode 36 toward the outer pumping electrode 34, depending upon a positive or negative oxygen concentration of the external measurement gas, that is, depending upon the selected position of the selection switch 48. Thus, the bidirectional pumping action of the pumping cell causes the oxygen in the thin flat space 32 to be pumped out into the external space, or causes the oxygen in the external space to be pumped into the thin flat space 32. The inner pumping electrode 36 is connected to current detecting means 50, so that a pumping current flowing between the two pumping electrodes 34, 36 is detected.

In the present embodiment, the inner pumping electrode 36 and the outer pumping electrode 34 are both electrically connected to a low-potential terminal of a heater power source 42, at a point of connection indicated at J in FIG. 4. In a line between the inner pumping electrode 36 and the connection point J, there is provided an auxiliary power source 52. Further, the first and second pump power sources 44, 46, which are connected in parallel connection with each other, are provided in a line between the outer pumping electrode 34 and the connection point J. In this arrangement, the potentials V11, V12 of the inner and outer pumping electrodes 36, 34 are maintained at positive values which satisfy the formula (2). Therefore, the electrochemical pumping cell may perform a bidirectional pumping operation with unipolar power source means, without deteriorating the heater layer 30 (electrically insulating ceramic layer 40) and spacer layer 28. It is noted that the pumping direction of the pumping cell, i.e., the direction of flow of the pumping current between the two pumping electrodes 34, 36 is established by suitably determining the potentials E2, E3 of the first and second pump power sources 44, 46, with respect to the potential E1 of the auxiliary power source 52.

Figure 6:
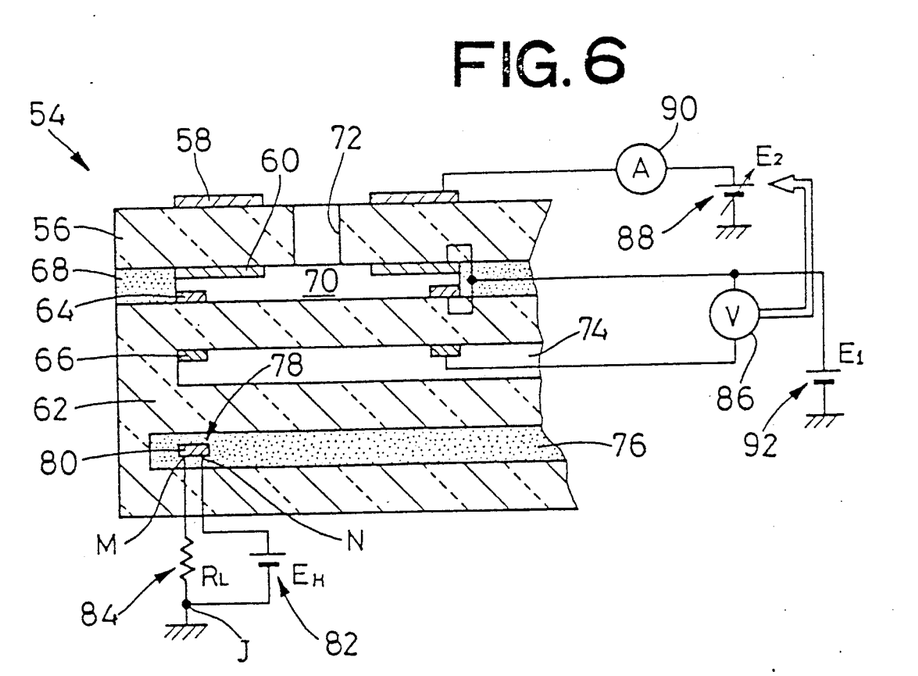
FIG. 6 is a schematic illlustration corresponding to that of FIG. 5, showing another embodiment of the invention.

Reference is now made to FIG. 6, which shows another embodiment of the electrochemical device incorporating an electrochemical element generally indicated at 54. Unlike the electrochemical element 22 of the device of FIG. 4, the electrochemical element 54 has two electrochemical cells, that is, an electrochemical pumping cell and an electrochemical sensing cell. This type of electrochemical cell is known as disclosed in U.S. Pat. Nos. 4,798,693 and 4,728,411, the disclosures of which are hereby incorporated by reference. It will be understood that the electrochemical element 54 may be modified according to the disclosures of the above-identified patents, without departing from the spirit and principle of the present invention.

The pumping cell of the electrochemical element 54 is constituted by a planar solid electrolyte body 56 made of stabilized zirconia, and an outer and an inner pumping electrode 58, 60, while the sensing cell is constituted by a planar solid electrolyte body 62 also made of stabilized zirconia, and a measuring and a reference electrode 64, 66. The pumping and sensing cells are superposed on each other via a second electrically insulating ceramic layer 68 interposed therebetween. The ceramic layer 68 has a thin round hole and cooperates with the upper and lower solid electrolyte planar solid electrolyte bodies 56, 62, to define a diffusion space in the form of a thin flat space 70, which has a predetermined diffusion resistance to the measurement gas. The inner pumping electrode 60 of the electrochemical pumping cell, and the measuring electrode 64 of the electrochemical sensing cell are formed on the respective solid electrolyte bodies 56, 62, such that the electrodes 60, 64 are exposed to the thin flat space 70. The solid electrolyte body 56 of the pumping cell has a gas inlet aperture 72 which communicates with the external space and the thin flat space 70, so that the external measurement gas is introduced through the aperture 72 and diffuses into the thin flat space 70 under the predetermined diffusion resistance, for contacting with the electrodes 60, 64.

The planar solid electrolyte body 62 of the sensing cell has a reference gas passage 74 for introducing a reference gas such as the ambient air to the reference electrode 66, which is exposed to the passage 74. The sensing cell incorporates therein a heat-generating portion 80 of a heater element 78. The heat-generating portion 80 is embedded in a first electrically insulating ceramic layer 76 formed of alumina integrally with the solid electrolyte body 62. The heat-generating portion 80 is connected to an external heater power source 82, so that the heat-generating portion 80 is energized to heat the pumping and sensing cells to suitable operating temperatures. A resistor 84 is connected between a low-potential terminal of the heater power source 82 and a low-potential terminal M of the heat-generating portion 80, such that an electrical resistance RL between these low-potential terminals is higher than an electrical resistance between a high-potential terminal of the power source 82 and a high-potential terminal N of the heat-generating portion 80.

In the electrochemical sensing cell, an electromotive force induced between the measuring and reference electrodes 64, 66 due to a difference between the oxygen concentrations of the measurement and reference gases is detected by voltage detecting means 86. In response to a change in the detected electromotive force, a potential E2 of a variable-voltage pump power source 88 is controlled to apply a controlled pumping current to the outer pumping electrode 58 of the pumping cell. The pumping current is detected by current detecting means 90 connected between the outer pumping electrode 58 and the pump power source 88.

In the instant embodiment, the four electrodes 58, 60, 64, 66 are formed on the surfaces of the solid electrolyte bodies 56, 62, and are electrically connected at a connection point J to the low-potential terminal of the heater power source 82. Since the second electrically insulating ceramic layer 68 is provided between the electrodes 58, 60 and the first electrically insulating ceramic layer 76, an electrical resistance between the electrodes 58, 60 and the first ceramic layer 76 is considerably high. Further, since the reference electrode 66 is connected to the connection point J of the low-potential terminal of the heater power source 82 via the voltage detecting means 88 which has a high input impedance, an electrical resistance between the reference electrode 66 and the low-potential terminal of the heater power source 82 is also considerably high. Consequently, influences of the potentials of these electrodes 58, 60, 66 on the potential of the solid electrolyte body 62 is almost negligible, and only the potential of the measuring electrode 64 should be taken into consideration. The measuring electrode 64 is connected directly to the low-potential terminal of the heater power source 82 because the electrode 64 and the low-potential terminal of the power source 82 are both grounded, as indicated in FIG. 6. Between the ground and the measuring electrode 64, there is provided an auxiliary power source 92 as voltage applying means for maintaining the potential of the measuring electrode 64 at a positive value according to the formula (1) indicated above. Namely, a positive potential E1 of the auxiliary power source 92 which satisfies the formula (1) is applied to the measuring electrode 64.

In the present electrochemical device of FIG. 6, too, a pumping current may flow between the two pumping electrodes 58, 60 in the opposite directions, by changing a potential E2 of the variable-voltage pump power source 88, within a positive range, as compared with the potential at the connection point J, which is higher or lower than the potential E1 of the auxiliary power source 92. In other words, the unipolar dc power source 88 permits a bi-directional pumping operation of the pumping cell. Further, the ceramic layer 76 and the solid electrolyte body 62 are effectively protected from deterioration, since the potential of the measuring electrode 64 is lower than the decomposition potentials of the ceramic layer 76 and solid electrolyte body 62, at their portions near the low-potential terminal M of the heat-generating portion 80 of the heater element 78.

An additional advantage of the present embodiment is derived from the provision of the resistor 84 between the low-potential terminal M of the heat-generating portion 80 and the low-potential terminal of the heater power source 82. In the presence of the resistor 84, an amount of voltage drop V2 between the low-potential terminal M and the connection point J (low-potential terminal of the power source 82) is increased, while preventing deterioration of the ceramic layer 76 and solid electrolyte body 62.

Figure 7:
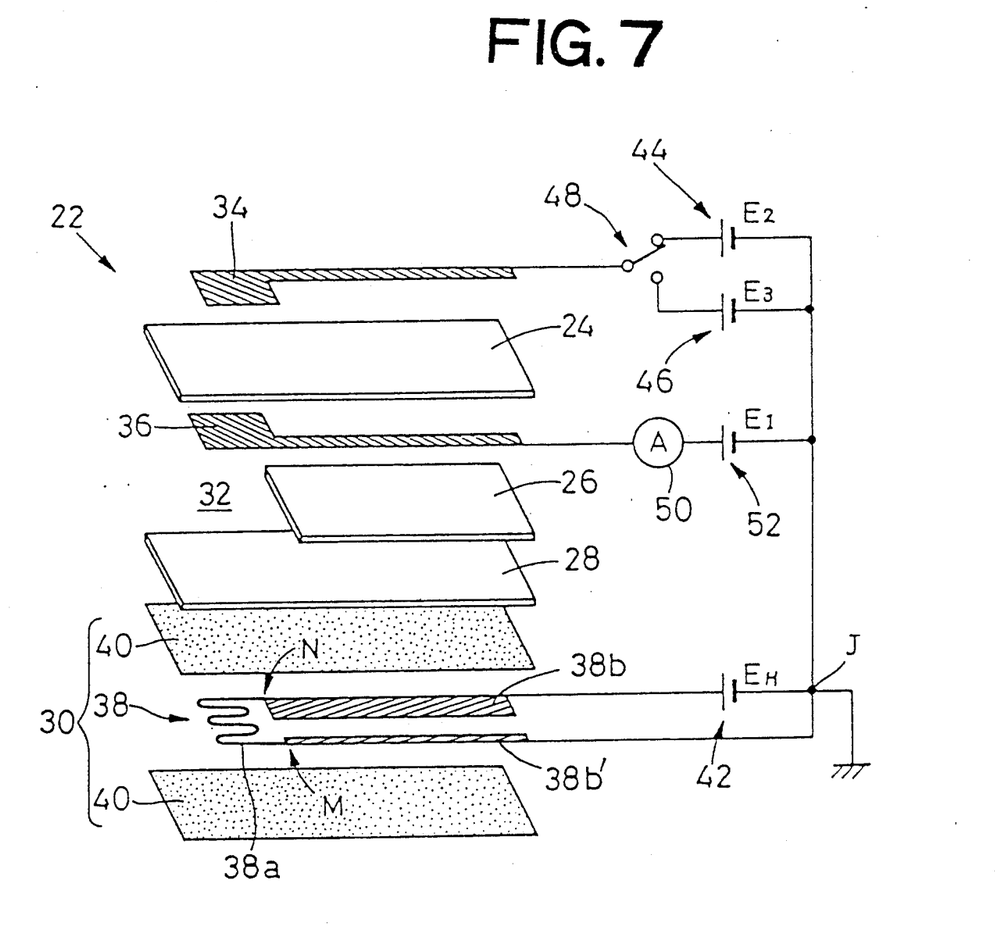
FIG. 7 is a schematic illustration corresponding to that of FIG. 4, showing a further embodiment of the invention.

A further embodiment of the present invention is illustrated in FIG. 7. This embodiment is identical with the embodiment of FIG. 4, except for the electrical leads $38b$, $38b'$ of the heater element 30. The same reference numerals as used in FIG. 4 are used in FIG. 7, to identify the same components.

In the embodiment of FIG. 4, the two electrical leads $38b$, $38'b$ of have the same electrical resistance values. In the embodiment of FIG. 7, however, the low-potential electrical lead $38b'$ of the heater element 30 has a higher resistance value than the high-potential electrical lead $38b$, so that a resistance between the low-potential terminal M of the heat-generating portion $38a$ and the connection point J of the low-potential terminal of the heater power source 42 is higher than that between the high-potential terminal N of the heat-generating portion $38a$ and the high-potential terminal of the heater power source 42.

The low-potential electrical lead $38b'$ of FIG. 7 having a higher electrical resistance performs the same function as a resistor as indicated at 84 in FIG. 6.

The operation, advantages and features of the electrochemical device according to the present invention will be further clarified from the following description of some experiments:

EXPERIMENT I

The electrochemical device shown in FIGS. 4 and 5 was prepared with the following specifications:

| | |
|---|---|
| EH of the power source 42 (Heater current IH = 0.8 A); | 12 V |
| E1 of the auxiliary power source 52 | 2.0 V |
| E2 of the first pump power source 44 | 2.7 V |
| E3 of the second pump power source 46 | 1.3 V |
| Potential of the low-potential terminal M | 0.9 V |

| |
|---|
| -continued |
| of the heat-generating portion 38a |

The solid electrolyte structure 26, 28 had an electrical resistance of 500Ω, as measured between the electrode 36 and the heater 38″ at 800° C. with an electrochemical element 22 without the electrically insulating ceramic layers 40, 40. The solid electrolyte structure 24, 26, 28 had an electrical resistance of 650 Ω, as measured in the same manner. The internal electrical resistances of the first and second pump power sources 44, 46 and auxiliary power source 52, and the input resistance of the current detecting means 50, were found negligibly low.

The electrochemical element 22 was exposed to a rich-burned exhaust gas which was produced as a result of combustion of a fuel-rich air-fuel mixture whose air/fuel ratio is smaller than the stoichiometric point. The selector switch 48 was set so as to apply a pumping voltage of $-0.7$ V (E3$-$E1) of the second pump power source 46 between the two pumping electrodes 34, 36, so that oxygen ions were pumped in the direction from the outer pumping electrode 34 toward the inner pumping electrode 36. As a result, the oxygen partial pressure in the thin flat space 32 to which the inner pumping electrode 36 is exposed was increased, and an electromotive force Ve2 of $-0.5$ V was detected between the two electrodes 34, 36. Thus, a weighted average of the potentials of the pumping electrodes 34, 36, which is obtained as follows, satisfies the formula (2).

$$\frac{650}{1150} \times 2.0 + \frac{500}{1150} (1.3 + 0.5) \leqq 1.4 + 0.9$$

This means that the potential of the solid electrolyte spacer member 28 with respect to that of the ceramic layer 40 may be maintained at a suitable level.

The electrochemical element 22 was also exposed to a lean-burned exhaust gas which was produced as a result of a fuel-lean air-fuel mixture whose air/fuel ratio is higher than the stoichiometric point. The selector switch 48 was set so as to apply a voltage of $+0.7$ V (E2$-$E1) of the first pump power source 44 between the two pumping electrodes 34, 36, so that the oxygen ions were pumped in the direction from the inner pumping electrode 36 toward the outer pumping electrode 34. As a result, the oxygen partial pressure in the thin flat space 32 to which the inner pumping electrode 36 is exposed was lowered, and an electromotive force Ve2 of $+0.5$ V was detected between the two electrodes 34, 36. Thus, a weighted average of the potentials of the pumping electrodes 34, 36, which is obtained as follows, satisfies the formula (2).

$$\frac{650}{1150} \times 2.0 + \frac{500}{1150} (2.7 - 0.5) \leqq 1.4 + 0.9$$

As is well known in the art, the air/fuel ratio of the air-fuel mixture involved may be determined by the amount of the pumping current which flows between the two pumping electrodes 34, 36.

According to the construction of the electrochemical device of FIGS. 4 and 5, there were prepared various specimen whose potentials E1 and E3 of the auxiliary and second pump power sources 52, 46 are indicated in Table 1, and wherein the potential EH of the heater power source 42 is 16 V. The specimen were subjected to durability tests with the cells and the heater element 30 kept energized for the periods indicated in Table 1. The measurement gas used was an exhaust gas produced as a result of combustion of a propane-rich, air-propane mixture whose excess air ratio was 0.8. The results of the durability tests are indicated in Table 1. The number of the fractured or cracked specimen of the five specimen which were subjected to each test is indicated in the table.

TABLE 1

| E1 | E3 | Continuous Energization Time | | |
|---|---|---|---|---|
|  |  | 120 Hr. | 240 Hr. | 500 Hr. |
| 0.8 V | 0.1 V | 0/5 | 0/5 | 0/5 |
| 2.0 V | 1.3 V | 0/5 | 0/5 | 0/5 |
| 4.0 V | 3.3 V | 2/5 | 5/5 | 5/5 |

It will be understood from Table 1 that the specimen of the electrochemical element 22 did not suffer from any defects where the weighted average potential of the pumping electrodes was lower than 2.3 V (potential at the low-potential terminal M of the heat-generating portion 38a + decomposition potential). Where the average potential was higher than 2.3 V, two of the five specimen cracked in the 120-hour test, while all the five specimen cracked in the 240-hour test.

EXPERIMENT II

The electrochemical device having the electrochemical element 54 shown in FIG. 6 was prepared with the following specifications:

| EH of the heater power source 82 | 12 V |
|---|---|
| IH of the heater power source 82 | 1.0 A |
| E1 of the auxiliary power source | 4.0 V |
| E2 of the variable-voltage pump power source | 1-7 V |
| RL of the resistor 84 | 2.0 Ω |
| Potential of the low-potential terminal M of the heat-generating portion 80 | 2.6 V |

The potential E2 of the variable-voltage pump power source 88 was changed so that an electromotive force induced in the electrochemical pumping cell was equal to 0.45 V.

The resistor 84 was provided by a lead wire which has the electrical resistance RL and which connects the low-potential lead of the heater element 80 and the low-potential terminal of the heater power source 82. The lead wire was a stranded stainless steel wire. The high-potential terminal of the heater power source 82 was connected to the high-potential lead of the heater element 80, by a 50 cm long, stranded Ni-plated copper wire which has an electrical resistance of 0.02Ω.

The specimen of the electrochemical device as described above were subjected to similar durability tests as in EXPERIMENT I. The tests revealed excellent durability of all specimens, without cracking after 200 hours of continuous energization of the electrochemical element 54.

EXPERIMENT III

The electrochemical element 22 of the device shown in FIG. 7 was prepared with the following specifications:

| E1 of the auxiliary power source 52 | 3.0 V |
|---|---|
| E2 of the first pump power source 44 | 3.7 V |
| E3 of the second pump power source 46 | 2.3 V |
| EH of the heater power source 42 | 12.0 V |

-continued

| Potential of the low-potential terminal M of the heat-generating portion 38a | 2.0 V |
|---|---|
| Potential of the high-potential terminal N of the heat-generating portion 38a | 11.6 V |

The specimen of the element 22 were subjected to similar durability tests as in EXPERIMENT I. The test revealed no cracking or other defects after 500 hours of continuous energization of the element 22. The average current applied to the heat-generating portion 38a of the heater layer 30 was 0.9 A, when the potential EH of the heater power source 42 was 12.0 V.

While the present invention has been described in its presently preferred forms and embodiments with a certain degree of particularity, it is to be understood that the invention is not limited to the details of the specific disclosures contained herein, but the invention may be embodied with various changes, modifications and improvements, which may occur to a person having ordinary skill in the art, without departing from the spirit and scope of the invention defined in the appended claims.

For instance, the solid electrolyte bodies, electrodes, electrically insulating ceramic layers and heater layer or heater element of the electrochemical element may be formed of suitable known materials other than those specified above. While stabilized zirconia may be particularly preferably used for the solid electrolyte bodies or layers, it is possible to use $SrCeO_3$, or a solid solution of $Bi_2O_3$ and oxides of rare earth. Further, the electrically insulating ceramic layers may be made of zirconia, mullite, spinel, titania, barium titanate, calcium zirconate, and other known insulating ceramic materials, other than alumina used in the illustrated embodiments. The ceramic layers may be formed by a known lamination or printing technique. The electrodes are desirably made of a metal selected from the platinum group which includes platinum, palladium and rhodium, or a mixture of the platinum group metal and a ceramic material such as zirconia and alumina. Of course, other suitable materials may be used for the electrodes.

What is claimed is:

1. An electrochemical device comprising:
   at least one oxygen-ion conductive solid electrolyte body;
   a plurality of electrodes formed on the solid electrolyte body;
   an electrically insulating ceramic layer formed on the solid electrolyte body;
   a heater disposed adjacent the ceramic layer so as to be electrically insulated from the solid electrolyte body;
   a dc power source electrically connected to the heater for energizing the heater, at least one of said plurality of electrodes being electrically connected to a low-potential terminal of said dc power source;
   at least one line connecting a corresponding one of said at least one electrode and said low-potential terminal of said dc power source; and
   voltage applying means provided in each said line, such that a potential V1 of said at least one electrode with respect to a potential at a point of connection of said line to said low-potential terminal of said dc power source is maintained at a positive value which satisfies the following formula:

$$V1 \leq V2 + V3$$

wherein V2 is a voltage drop between a low-potential terminal of a heat-generating portion of said heater and said point of connection to said low-potential terminal of said dc power source, which occurs due to a heating current applied to said heat generating portion, and V3 is a decomposition voltage of said ceramic layer or the solid electrolyte body, whichever is lower, wherein said at least one electrode operates as an anode.

2. The electrochemical device of claim 1, further comprising resistor means provided between said low-potential terminal of said heat-generating portion of said heater and said point of connection of said line to said low-potential terminal of said dc power source, so that a value of electrical resistance between said low-potential terminal of said heat-generating portion and said point of connection of said line to said low potential terminal of said dc power source is higher than that between a high-potential terminal of said heat-generating portion and a high-potential terminal of said dc power source.

3. The electrochemical device of claim 2, wherein said heater includes a low-potential electrical lead which connects said low-potential terminals of said heat-generating portion and said dc power source, and a high-potential electrical lead which connects said high-potential terminals of said heat-generating portion and said dc power source, said low-potential electrical lead having a higher electrical resistance than said high-potential electrical lead, and thereby serving as said resistor means.

4. The electrochemical device of claim 1, wherein said plurality of electrodes consist of two electrodes which are both electrically connected to said low-potential terminal of said dc power source.

5. The electrochemical device of claim 1, further comprising a second electrically insulating ceramic layer which separates the solid electrolyte body into two parts, and said plurality of electrodes consist of three electrodes, of which two electrodes are formed on one of opposite surfaces of one of said two parts of the solid electrolyte body, which one surface of said one part is remote from said second electrically insulating ceramic layer, and one protective electrode is formed on one of opposite surfaces of the other part of said solid electrolyte body such that said one protective electrode is covered by said second electrically insulating ceramic layer, wherein said two electrodes are electrically connected to said low-potential terminal of said dc power source via said voltage applying means, while said protective electrode is electrically connected to said low-potential terminal of said dc power source via an auxiliary power source.

6. The electrochemical device of claim 1, wherein said voltage applying means comprises two voltage dividing resistors connected to said low-potential terminal and a high-potential terminal of said dc power source, said line including one of said two voltage dividing resistors which is connected to said low-potential terminal of said dc power source.

7. The electrochemical device of claim 1, wherein said plurality of electrodes include an outer and and an inner pumping electrode which are formed on opposite surfaces of the solid electrolyte body such that said outer pumping electrode is exposed to a measurement gas in an external space, and the solid electrolyte body at least partially defines a diffusion space to which said inner pumping electrode is exposed and which has a predetermined diffusion resistance to said measurement gas, said electrochemical device further comprising a first and a second pump power source, and a selector switch for selectively connecting said first pump power source and said second pump power source to said outer pumping electrode and said inner pumping electrode, said low-potential terminal of said dc power source for said heater being connected to said outer pumping electrode and said inner pumping electrode, and said voltage applying means being provided in a line between said point of connection to said low-potential terminal of said dc power source and said inner pumping electrode.

8. The electrochemical device of claim 1, wherein the solid electrolyte body includes a first and a second solid electrolyte body which are electrically insulated from each other by a second electrically insulating ceramic layer, such that said first solid electrolyte body, said second solid electrolyte body and said second electrically insulating ceramic layer cooperate with each other to define a diffusion space which has a predetermined diffusion resistance to a measurement gas, said first solid electrolyte body having a gas inlet aperture for introducing said measurement gas from an external space into said diffusion space, and said second solid electrolyte body having a reference gas passage in which a reference gas exists, said plurality of electrodes including an outer pumping electrode and an inner pumping electrode, a measuring electrode and a reference electrode, said outer pumping electrode and said inner pumping electrode being formed on opposite major surfaces of said first solid electrolyte body such that said outer pumping electrode is exposed to said measurement gas in said external space, while said inner pumping electrode is exposed to said diffusion space, said measuring electrode and said reference electrode being formed on opposite surfaces of said second solid electrolyte body such that said measuring electrode is exposed to said diffusion space while said reference electrode is exposed to said reference gas passage, and wherein said measuring electrode is electrically connected to said low-potential terminal of said dc power source via said voltage applying means.

9. The electrochemical device of claim 8, wherein said low-potential terminal of said dc power source and a low-potential terminal of said voltage applying means are both grounded.

10. The electrochemical device of claim 8, further comprising a variable-voltage pump power source connected to said outer pumping electrode, and voltage detecting means connected between said measuring electrode and said reference electrode, for detecting an electromotive force induced between said measuring electrode and reference electrode, a voltage of said variable-voltage pump power source being controlled in response to said electromotive force detected by said voltage detecting means.

\* \* \* \* \*